US010937152B2

(12) United States Patent
Segawa

(10) Patent No.: US 10,937,152 B2
(45) Date of Patent: Mar. 2, 2021

(54) INSPECTION SUPPORT METHOD AND INSPECTION SUPPORT DEVICE

(71) Applicant: FUJIFILM Corporation, Tokyo (JP)

(72) Inventor: Hideo Segawa, Ashigarakami-gun (JP)

(73) Assignee: FUJIFILM Toyama Chemical Co., Ltd., Tokyo (JP)

( * ) Notice: Subject to any disclaimer, the term of this patent is extended or adjusted under 35 U.S.C. 154(b) by 105 days.

(21) Appl. No.: 16/165,125

(22) Filed: Oct. 19, 2018

(65) Prior Publication Data

US 2019/0050977 A1 Feb. 14, 2019

Related U.S. Application Data

(63) Continuation of application No. PCT/JP2017/014262, filed on Apr. 5, 2017.

(30) Foreign Application Priority Data

Apr. 22, 2016 (JP) .............................. JP2016-086312

(51) Int. Cl.
*G06K 9/00* (2006.01)
*G06T 7/00* (2017.01)
(Continued)

(52) U.S. Cl.
CPC ................. *G06T 7/001* (2013.01); *A61J 1/10* (2013.01); *A61J 3/00* (2013.01); *G06K 9/00* (2013.01);
(Continued)

(58) Field of Classification Search
None
See application file for complete search history.

(56) References Cited

U.S. PATENT DOCUMENTS 6,330,351 B1 12/2001 Yasunaga
8,055,512 B1 * 11/2011 Pankow ................. G06Q 50/22
705/2
(Continued)

FOREIGN PATENT DOCUMENTS

CN 104582670 A 4/2015
EP 2 591 761 A1 5/2013
(Continued)

OTHER PUBLICATIONS

Communication dated Jun. 24, 2019, from the Japanese Patent Office in counterpart application No. 2016-086312.
(Continued)

*Primary Examiner* — Shervin K Nakhjavan
(74) *Attorney, Agent, or Firm* — Sughrue Mion, PLLC

(57) ABSTRACT

An object of the present invention is to provide an inspection support method and an inspection support device capable of easily inspecting packaged medicines. In accordance with the inspection support method and the inspection support device according to an aspect of the present invention, since images of packaged medicines and identification information items and quantities of medicines extracted from a prescription are displayed on a display device (display unit), a user can easily check whether or not the packaged medicines match those written in the prescription. Since master images are registered in a case where the determination of "whether or not identification information items and quantities of the packaged medicines match the identification information items and quantities which are extracted from the prescription and are displayed" is positive for all the medicines written in the prescription, it is possible to reduce a concern that inappropriate images will be registered as the master images. It is easy to align imaging conditions (Continued)

between the master images and collating target images, and it is possible to increase collation accuracy.

7 Claims, 11 Drawing Sheets

(51) Int. Cl.
  *G06K 9/62* (2006.01)
  *A61J 3/00* (2006.01)
  *G16H 20/13* (2018.01)
  *A61J 1/10* (2006.01)

(52) U.S. Cl.
  CPC ......... *G06K 9/6253* (2013.01); *G06K 9/6255* (2013.01); *G16H 20/13* (2018.01); *A61J 2200/70* (2013.01); *G06T 2207/20092* (2013.01); *G06T 2207/30108* (2013.01)

(56) References Cited

U.S. PATENT DOCUMENTS

| | | | |
|---|---|---|---|
| 9,272,796 B1* | 3/2016 | Chudy | B65B 5/103 |
| 2004/0017475 A1* | 1/2004 | Akers | G06Q 50/22 |
| | | | 348/207.1 |
| 2004/0088187 A1* | 5/2004 | Chudy | G06Q 10/10 |
| | | | 705/2 |
| 2005/0240523 A1* | 10/2005 | Richardson | G06Q 20/102 |
| | | | 705/40 |
| 2006/0060645 A1* | 3/2006 | Udaka | G06F 19/3462 |
| | | | 235/375 |
| 2011/0184751 A1* | 7/2011 | Holmes | B65B 57/00 |
| | | | 705/2 |
| 2011/0202366 A1* | 8/2011 | Akers | G16H 10/60 |
| | | | 705/2 |
| 2012/0200596 A1 | 8/2012 | Gotou et al. | |
| 2013/0194414 A1* | 8/2013 | Poirier | G06K 9/64 |
| | | | 348/92 |
| 2015/0170373 A1* | 6/2015 | Yonaha | G06F 19/3462 |
| | | | 382/143 |
| 2015/0178674 A1* | 6/2015 | Yonaha | G06Q 10/087 |
| | | | 705/2 |
| 2016/0005160 A1 | 1/2016 | Ito et al. | |
| 2016/0163034 A1* | 6/2016 | Jacobs | G06T 7/0004 |
| | | | 382/142 |
| 2016/0259914 A1* | 9/2016 | Iantorno | G16H 20/13 |
| 2018/0170591 A1* | 6/2018 | Koike | B65B 9/067 |

FOREIGN PATENT DOCUMENTS

| | | |
|---|---|---|
| JP | H09-256163 A | 9/1997 |
| JP | 10162116 A | 6/1998 |
| JP | 2000276583 A | 10/2000 |
| JP | 2008018230 A | 1/2008 |
| JP | 2014067342 A | 4/2014 |
| JP | 2014221134 A | 11/2014 |
| WO | 2012005004 A1 | 1/2012 |
| WO | 2014/080966 A1 | 5/2014 |
| WO | 2015021442 A1 | 2/2015 |

OTHER PUBLICATIONS

Communication dated Mar. 29, 2019 from European Patent Office in counterpart EP Application No. 17785801.6.
Notice of Reasons for Refusal dated Nov. 21, 2019 issued by the Japanese Patent Office in counterpart application No. 2016-086312.
Communication dated Sep. 7, 2020, issued by the European Patent Office in application No. 17 785 801.6.
Communication dated Jul. 6, 2020, issued by the State Intellectual Property Office of the P.R.C. in application No. 201780024785.8.
International Preliminary Report on Patentability and Translation of Written Opinion, dated Oct. 23, 2018 from the International Bureau in counterpart International application No. PCT/JP2017/014262.
Written Opinion, dated Jul. 4, 2017 from the International Bureau in counterpart International application No. PCT/JP2017/014262.
International Search Report, dated Jul. 4, 2017 from the International Bureau in counterpart International application No. PCT/JP2017/024262.
Office Action dated Jun. 2, 2020 in Japanese Application No. 2016-086312.

* cited by examiner

FIG. 12

PATIENT NAME: TARO FUJI

FIRST PACKAGING BAG: FRONT

FIRST PACKAGING BAG: REAR

PRESCRIPTION

THREE TIMES A DAY AFTER MEAL

MEDICINE A TWO TABLETS — INFORMATION DISPLAY — EDIT

MEDICINE B ONE TABLET — INFORMATION DISPLAY — EDIT

CONFIRMATION  ABORT

MEDICINE IMAGE

FRONT  REAR

INSPECTION SUPPORT METHOD AND INSPECTION SUPPORT DEVICE

CROSS-REFERENCE TO RELATED APPLICATIONS

The present application is a Continuation of PCT International Application No. PCT/JP2017/014262 filed on Apr. 5, 2017 claiming priority under 35 U.S.C § 119(a) to Japanese Patent Application No. 2016-086312 filed on Apr. 22, 2016. Each of the above applications is hereby expressly incorporated by reference, in their entirety, into the present application.

BACKGROUND OF THE INVENTION

1. Field of the Invention

The present invention relates to a medicine inspection support method and a medicine inspection support device, and particularly, to an inspection support method and an inspection support device that support inspection of whether or not packaged medicines match medicines written in a prescription.

2. Description of the Related Art

In general, a patient goes to a pharmacy with a prescription written by a doctor and medicines are dispensed in the pharmacy according to the prescription in a medical field. A so-called "packaging" for packaging the prescribed medicines for every single dosage is performed at the time of dispensing the medicines. The medicines are packaged in this manner, and thus, an effect of preventing the patient from forgetting to take the medicines, easily taking out the medicines from the packaging bag, or easily managing the taking of the medicines is expected.

Meanwhile, in a case where a pharmacist dispenses the medicines or provides the medicines, there is a need for the prescribed contents to be checked based on items or patient information written in the prescription. Thus, since the pharmacist needs to check the usage directions for every single dosage in inspecting the packaged medicines, an inspection burden of the pharmacist increases. Thus, in order to reduce the inspection burden of the pharmacist, an inspection support method and an inspection support device that collate the contents written in the prescription with the contents of the packaged medicines for the colors, sizes, shapes, and quantities of the medicines have been developed. For example, in a technology described in JP2014-067342A, a list is created by extracting medicine information items from a prescription and collating medicine master images of the extracted medicines with captured images. In a technology described in JP2008-018230A, collation of whether or not medicines of each packaging bag match medicines written in a prescription is performed by collating master images of a first packaging bag with images of the next packaging bag.

SUMMARY OF THE INVENTION

In JP2014-067342A, a method of obtaining or generating the medicine master images is not sufficiently considered. For example, images of medicines provided by a pharmaceutical company may be used as the master images. However, imaging conditions (lighting and exposing conditions, backgrounds of the medicines, and imaging magnifications) of the master images provided by the pharmaceutical company and imaging conditions at the time of inspecting the medicines in the pharmacy may not necessarily match each other, and there is a concern that collation accuracy will be reduced by using the images compared under the different imaging conditions. JP2008-018230A assumed that the first packaging bag among the packaging bags of the medicines is correctly packaged, but does not describe a method of performing the collation for the first packaging bag. Since a wide variety of medicines are treated in the pharmacy, there is a concern that the collation for the packaging bags of the medicines will lead to an increase in burden of the user (pharmacist) and inappropriate images will be used as the master images in a case where there is an error in the collation. As stated above, it is difficult to reduce the inspection burden of the pharmacist in the related art.

The present invention has been made of such circumstances, and an object of the present invention is to provide an inspection support method and an inspection support device capable of easily inspecting packaged medicines.

In order to achieve the aforementioned object, according to a first aspect of the present invention, there is an inspection support method comprising a first image obtaining step of obtaining first images which are images of packaged medicines, an information extracting step of extracting identification information items and quantities of medicines written in a prescription, a display step of displaying the obtained first images and the extracted identification information items and quantities on a display device, a determination step of determining whether or not identification information items and quantities of the packaged medicines match the displayed identification information items and quantities based on an instruction input of a user, a master image registering step of registering the first images as master images in a case where the determination result is positive for all the medicines written in the prescription, and a collation step of collating whether or not the medicines packaged in each packaging bag match the medicines written in the prescription based on the registered master images and second images which are images obtained for each packaging bag.

According to the first aspect, since the first images which are the images of the packaged medicines and the identification information items and quantities of the medicines extracted from the prescription are displayed on the display device, the user (pharmacist) can easily check whether or not the packaged medicines match those written in the prescription. In a case where the determination of "whether or not the identification information items and quantities of the packaged medicines match the identification information items and quantities which are extracted from the prescription and are displayed" is positive for all the medicines written in the prescription, since the first images are registered as the master images, it is possible to reduce a concern that inappropriate images will be registered as the master images. Since the first images obtained in the first image obtaining step are registered as the master images in the aforementioned case, it is easy to align imaging conditions between the master images and the second images (collating target images), and it is possible to increase collation accuracy.

As stated above, according to the first aspect, it is possible to easily inspect the packaged medicines. In the first aspect, the images registered as the master images may be images for the first packaging bag, or may be images for the second or subsequent packaging bag.

According to a second aspect, the inspection support method according to the first aspect further comprises a storing step of storing the images and the identification information items in association with each other for the medicines included in the inspected packaging bag in a first storage device, and a medicine image obtaining step of obtaining the images of the medicines written in the prescription while referring to the first storage device based on the extracted identification information items. The images obtained in the medicine image obtaining step are displayed in the display step. According to the second aspect, since the images of the medicines included in the inspected packaging bag are displayed in the display step, the user (pharmacist) can more easily check whether or not the packaged medicines match those written in the prescription by referring to the displayed images, and it is possible to reduce a concern that the inappropriate images will be registered as the master images. In the second aspect, the storing of the images in the storing step and the obtaining of the images in the medicine image obtaining step may be performed for each medicine.

According to a third aspect, the inspection support method according to the first or second aspect further comprises an attribute information obtaining step of obtaining attribute information items of the medicines written in the prescription while referring to a second storage device that stores the attribute information items of the medicines based on the extracted identification information items. The obtained attribute information items are displayed on the display device in the display step. According to the third aspect, the attribute information items of the medicines written in the prescription are obtained based on the identification information items of the medicines, and the obtained attribute information items are displayed on the display device. By doing this, the user (pharmacist) can more easily check whether or not the packaged medicines match those written in the prescription by referring to the displayed attribute information items, and it is possible to reduce a concern that the inappropriate images will be registered as the master images.

According to a fourth aspect, in the inspection support method according to the third aspect, the attribute information includes at least one of a medicine type, a shape, a dimension, a color, or a stamp of the medicine. The fourth aspect shows a specific example of the attribute information.

According to a fifth aspect, in the inspection support method according to any one of the first to fourth aspects, a plurality of images obtained by imaging the packaged medicines in a plurality of different directions is obtained as the first images in the first image obtaining step, and the plurality of images obtained as the first images is displayed in the display step. According to the fifth aspect, even in a case where it is difficult to perform collation due to the orientation or overlap of the medicines within the packaging bag, since the images obtained by imaging the packaged medicines in the plurality of different directions are displayed, the user (pharmacist) can easily check whether or not the packaged medicines match those written in the prescription while referring to the displayed images, and it is possible to reduce a concern that the inappropriate images will be registered as the master images.

According to a sixth aspect, the inspection support method according to any one of the first to fifth aspects further comprises a warning step of outputting a warning in a case where the collation in the collation step is not able to be performed and the medicines packaged in each packaging bag do not match the medicines written in the prescription as the result of the collation. The warning is output as in the sixth aspect, and thus, it is possible to reduce a concern that the inappropriate images will be registered as the master images. The outputting of the warning can be performed by information items such as voice, characters, symbols, and light, and combinations thereof.

In addition to the inspection support method according to the first to sixth aspects, an inspection support program causing an inspection support device to perform the inspection support method according to these aspects and a non-transitory recording medium that records computer-readable codes of the inspection support program may also be an aspect of the present invention. Examples of the non-transitory recording medium include an optical disk such as a compact disk (CD) or a digital versatile disk (DVD), a magnetic recording device such as a hard disk (HD), and various semiconductor recording media, and are not limited thereto.

In order to achieve the aforementioned object, according to a seventh aspect, there is provided an inspection support device comprising a first image obtaining unit that obtains first images which are images of packaged medicines, an information extracting unit that extracts identification information items and quantities of medicines written in a prescription, a display unit that displays the obtained first images and the extracted identification information items and quantities, a determination unit that determines whether or not identification information items and quantities of the packaged medicines match the displayed identification information items and quantities based on an instruction input of a user, a master image registering unit that registers the first images as master images in a case where the determination result is positive for all the medicines written in the prescription, and a collation unit that collates whether or not the medicines packaged in each packaging bag match the medicines written in the prescription based on the registered master images and second images which are images obtained for each packaging bag. In the seventh aspect, it is possible to easily inspect the packaged medicines similarly to the first aspect. In the seventh aspect, the inspection support device can further comprise the same configurations as those of the second to sixth aspects.

As described above, in accordance with the inspection support method and the inspection support device according to the embodiment of the present invention, it is possible to easily inspect the packaged medicines.

BRIEF DESCRIPTION OF THE DRAWINGS

FIG. 12 is a diagram showing still another example of the master image registering screen.

DESCRIPTION OF THE PREFERRED EMBODIMENTS

Hereinafter, an embodiment of an inspection support method and an inspection support device according to an embodiment of the present invention will be described with reference to the accompanying drawings.

<Configuration of Inspection Support Device>

Figure 1:
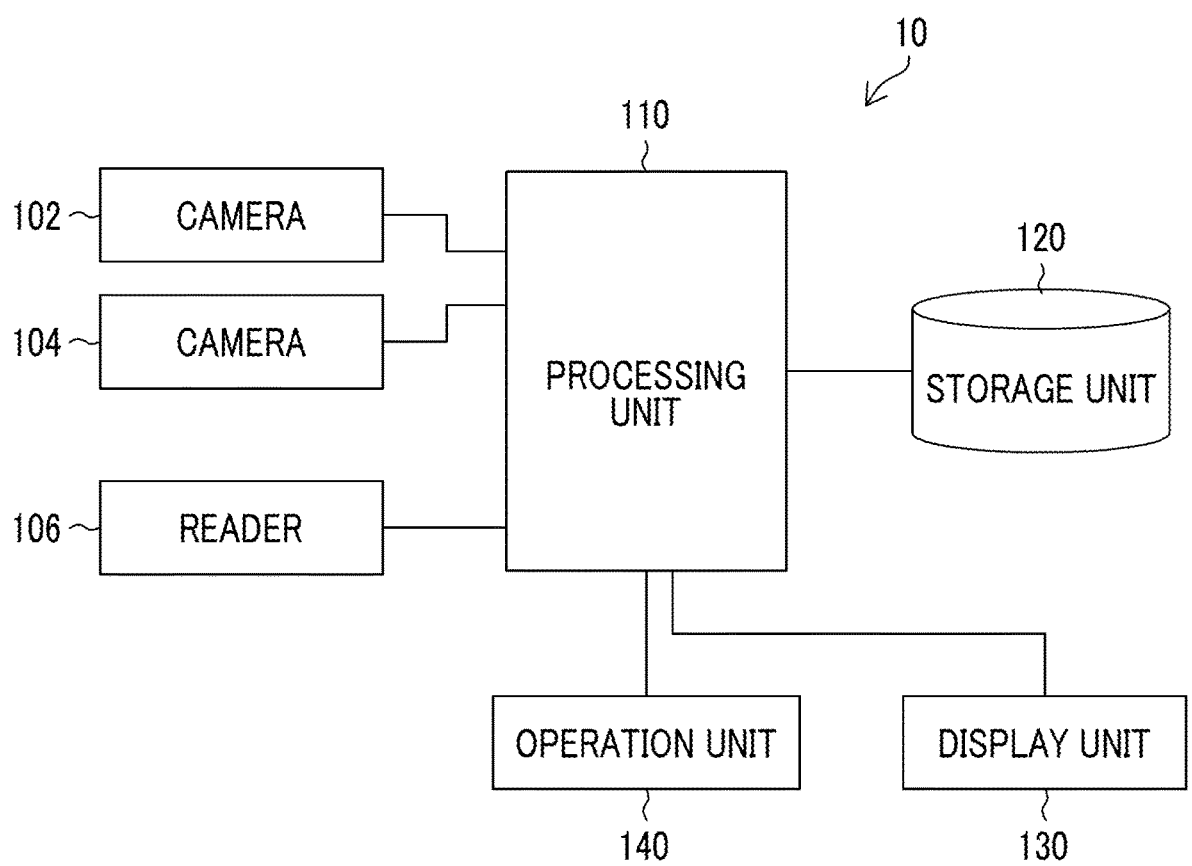
FIG. 1 is a diagram showing a configuration of an inspection support device according to an embodiment of the present invention.

FIG. 1 is a diagram showing a configuration of an inspection support device 10 according to the embodiment of the present invention. The inspection support device 10 comprises a processing unit 110, a storage unit 120, a display unit 130, and an operation unit 140, and a camera 102, a camera 104, and a reader 106 are connected to the processing unit 110. The inspection support device 10 comprises a packaging bag transport mechanism (not shown) in addition to these units.

The camera 102 and the camera 104 are digital cameras, and image medicines packaged in a packaging bag. The camera 102 is disposed on an upper side in a transport direction of the packaging bag and the camera 104 is disposed on a lower side in the transport direction such that the packaged medicines can be captured in a plurality of different directions.

The reader 106 reads prescription information. For example, the reader reads information items of a patient name, prescribed medicines, and quantities thereof from the prescription written on the paper through optical character recognition (OCR). In a case where a barcode indicating information regarding the prescribed medicines is recorded in the prescription, the barcode may be read, and thus, the information items of the prescribed medicines and the quantities thereof may be read. A user may read the prescription, and may input the prescription information by using an input device such as a keyboard of the operation unit 140.

<Configuration of Processing Unit>

Figure 2:
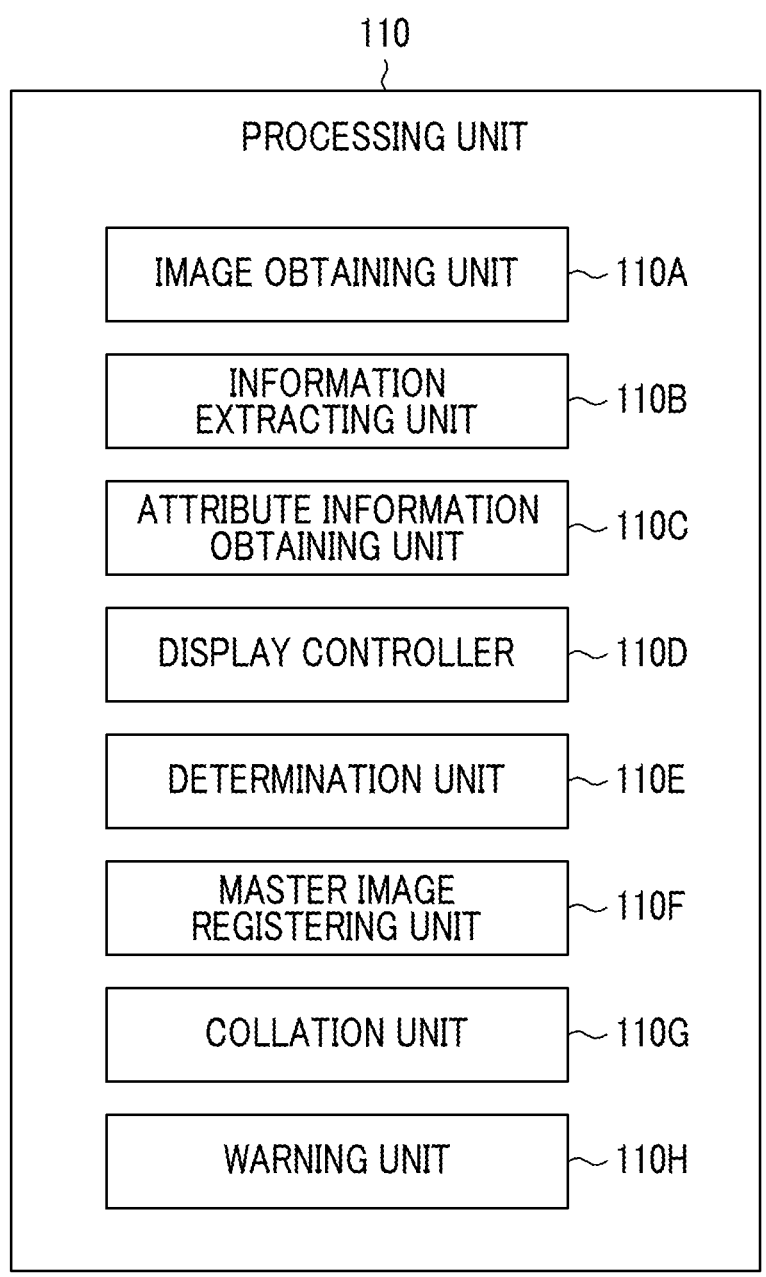
FIG. 2 is a diagram showing a functional configuration of a processing unit.

FIG. 2 is a diagram showing a major functional configuration of the processing unit 110. The processing unit 110 comprises an image obtaining unit 110A, an information extracting unit 110B, an attribute information obtaining unit 110C, a display controller 110D, a determination unit 110E, a master image registering unit 110F, a collation unit 110G, and a warning unit 110H. A device such as a central processing unit (CPU) or various electronic circuits executes an inspection support program stored in a read-only memory (ROM: non-transitory recording medium) while referring to data stored in Electrically Erasable and Programmable Read-Only Memory (EEPROM: non-transitory recording medium), and thus, these functions (processes of the inspection support method) are performed. A temporary storage area or a work area is used as a random-access memory (RAM) at the time of performs the processes. In FIG. 2, the illustration of these devices will be omitted.

The image obtaining unit 110A controls the camera 102 and the camera 104 obtains images of the medicines packaged in the packaging bag. The camera 102, the camera 104, and the image obtaining unit 110A constitute a first image obtaining unit. The information extracting unit 110B extracts patient information such as a name, and identification information items and quantities of the prescribed medicines from the prescription information read by the reader 106. The reader 106 and the information extracting unit 110B constitute an information extracting unit. The attribute information obtaining unit 110C obtains attribute information items of the medicines while referring to the storage unit 120 (attribute information 120D). The display controller 110D controls the display unit 130 to display. The determination unit 110E (determination unit) determines whether or not the identification information items and quantities of the packaged medicines match identification information items and quantities displayed on the display unit 130 based on an instruction input of the user. In a case where the determination result of the determination unit 110E is positive for all medicines written in the prescription, the master image registering unit 110F registers the images of the medicines packaged in the packaging bag as master images (master images 120A; see FIG. 3) in the storage unit 120. In this case, the master image registering unit 110F also stores images (medicine images 120B; see FIG. 3) of the individual medicines in the storage unit 120. The collation unit 110G (collation unit) collates whether or not the medicines packaged in each packaging bag are the medicines written in the prescription based on the images of the medicines packaged in each packaging bag and the master images. In a case where it is not possible to collate the images of the packaged medicines with the master images and it is determined that the medicines packaged in each packaging bag are not the medicines written in the prescription as the result of the collation, the warning unit 110H (warning unit) outputs a warning. The processing unit 110 has a function required to perform the processes in the inspection support device 10 in addition to the aforementioned primary functions.

The details of the processes using the processing unit 110 having the aforementioned configuration will be described below.

<Configuration of Storage Unit>

Figure 3:
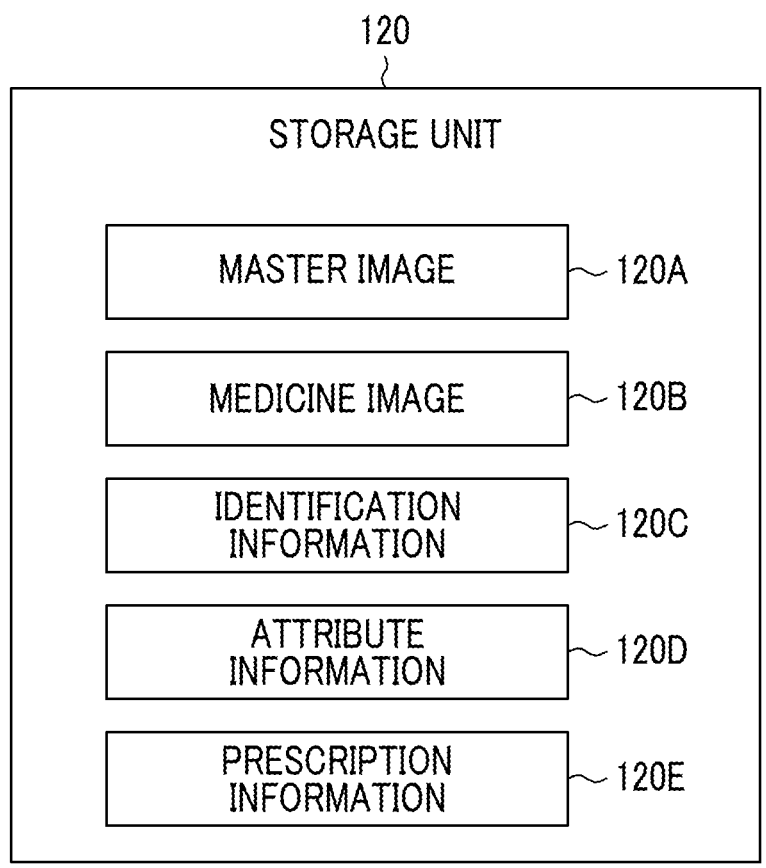
FIG. 3 is a diagram showing information items stored in a storage unit.

The storage unit 120 (first storage device or second storage device) is a non-transitory recording medium such as a compact disk (CD), a digital versatile disk (DVD), a hard disk, or various semiconductor memories, and stores the images and the information items shown in FIG. 3 in association with each other. In a case where it is checked that the packaged medicines are those written in the prescription, the master images 120A are obtained by registering images (an image including a plurality of medicines in some cases) for each packaging bag as a reference of the collation. Similarly, in a case where it is checked that the packaged medicines are those written in the prescription, the medicine images 120B are obtained by registering images of the individual medicines. The identification information 120C is information for uniquely identifying the medicine. For example, the name, ingredient quantity, and pharmaceutical company name of the medicine may be used as the identification information. Various pharmaceutical codes such as a so-called "YJ code (medicine price information code) may be used as the identification information. The attribute information 120D is information indicating the attribute of the medicine. A medicine type, shape, dimension, color, and stamp of the medicine are used as the attribute information in the present embodiment, but the present invention is not limited thereto. The prescription information 120E is obtained by storing information read by the reader 106, and includes the patient name, the identification information items and quantities of the medicines, and the usage directions.

At the time of performing the processes using the processing unit 110, the aforementioned image or information is read or written between the processing unit 110 and the storage unit 120.

<Configurations of Display Unit and Operation Unit>

The display unit 130 (display unit or display device) may comprise a display device such as a liquid crystal display, and may display the images of the packaged medicines, the identification information items (identification information 120C) and the images (the master images 120A and the medicine images 120B) of the medicines stored in the storage unit 120, and the prescription information (prescription information 120E). The operation unit 140 includes a pointing device such as a mouse and an input device such as a keyboard, and the user can operate an image or a button displayed on the display unit 130 by using the operation unit 140.

<Processes of Inspection Support Method>

Figure 4:
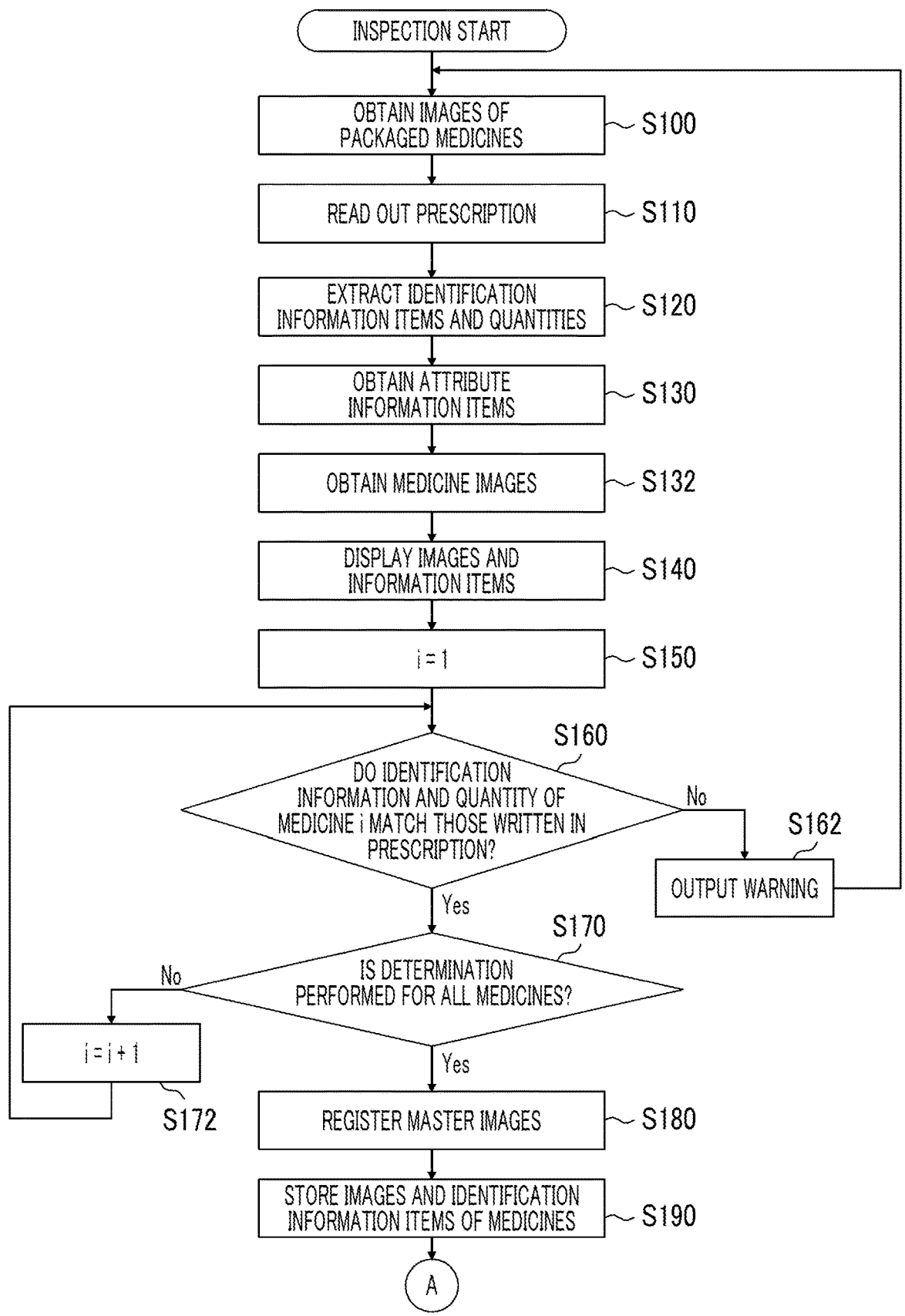
FIG. 4 is a flowchart showing a processing procedure in the inspection support device.
Figure 5:
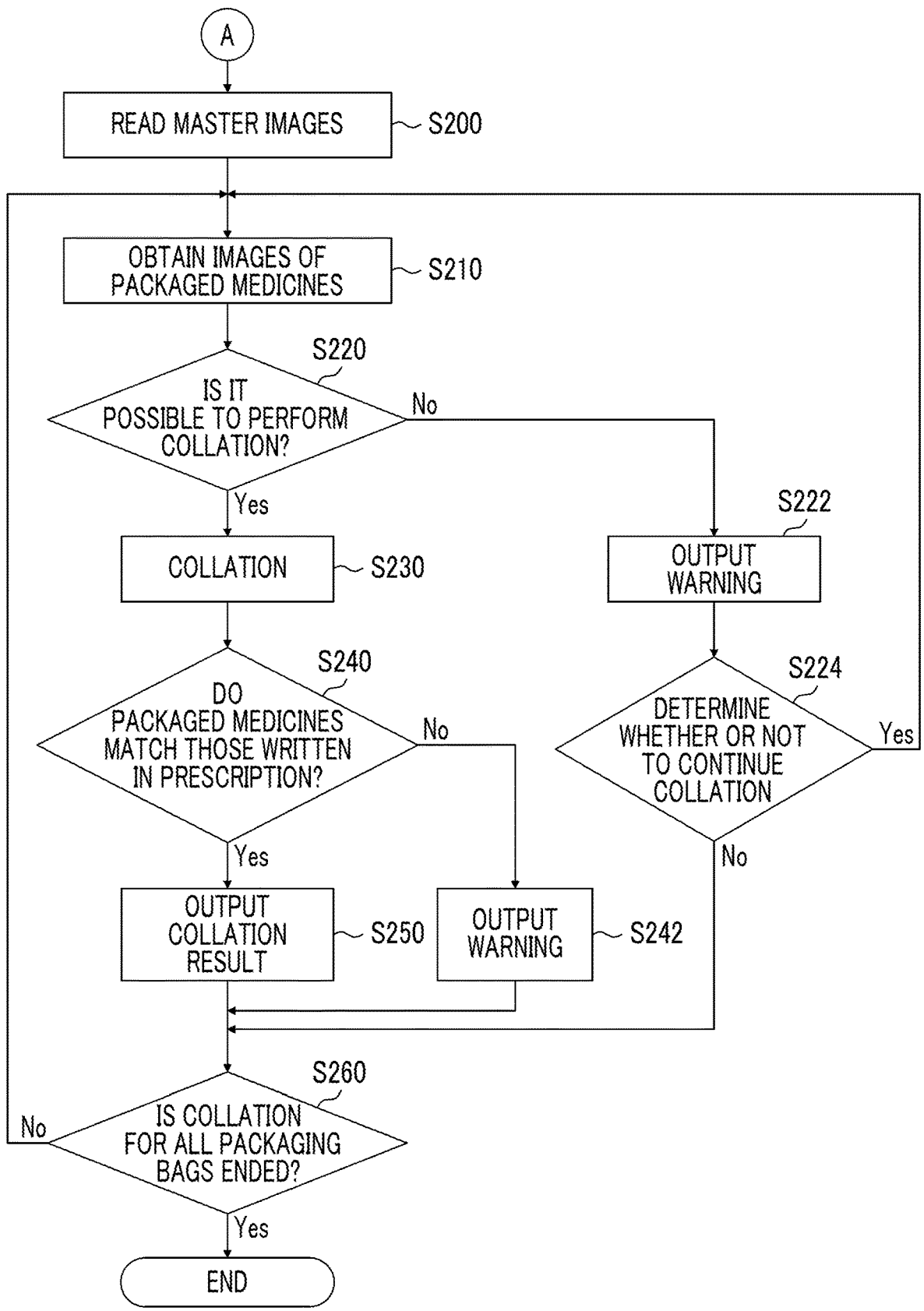
FIG. 5 is a flowchart (subsequent to FIG. 4) showing the processing procedure in the inspection support device.

Next, the processes of the inspection support method using the inspection support device 10 having the aforementioned configuration will be described. FIGS. 4 and 5 are flowcharts showing the processes of the inspection support method. In the processes shown in FIGS. 4 and 5, it is assumed that the medicines are packaged in each of the continuous packaging bags according to the prescription and the packaging bags are transported by a packaging bag transport mechanism. In conjunction with the transport, the camera 102 obtains an image of the medicines from above each packaging bag, and the camera 104 obtains an image of the medicines from below each packaging bag.

In a case where the process is started, the processing unit 110 (the image obtaining unit 110A) obtains the images of the medicines from above or from below of the packaging bags by the camera 102 and the camera 104 (step S100: first image obtaining step). The obtained images are displayed on the display unit 130 (to be described below).

Subsequently, the processing unit 110 (the information extracting unit 110B) reads out the prescription by the reader 106 (step S110), and the information extracting unit 110B extracts the patient name, the identification information items and quantities of the medicines, and the usage directions written in the prescription (step S120: information extracting step). The processing unit may read the prescription information 120E which is read in advance and is stored in the storage unit 120, and may use the read prescription information. The identification information may be information, such as the names and active ingredient quantities of the medicines, capable of specifying the medicines, and may be the pharmaceutical code such as the YJ (medicine price information) code.

The attribute information obtaining unit 110C obtains the attribute information items of the medicines written in the prescription while referring to the storage unit 120 (attribute information 120D) based on the identification information items extracted in step S120 (step S130: attribute information obtaining step). The image obtaining unit 110A obtains the images (the images of the inspected medicine) of the medicines written in the prescription while referring to the storage unit 120 (medicine image 120B) based on the identification information items extracted in step S120 (step S132: medicine image obtaining step).

Subsequently, the display controller 110D displays the image and the information obtained in step S100 to step S132 on the display unit 130 (step S140: display step). The user checks whether or not the medicines packaged in the packaging bags match those written in the prescription through a displayed screen.

Figure 6:
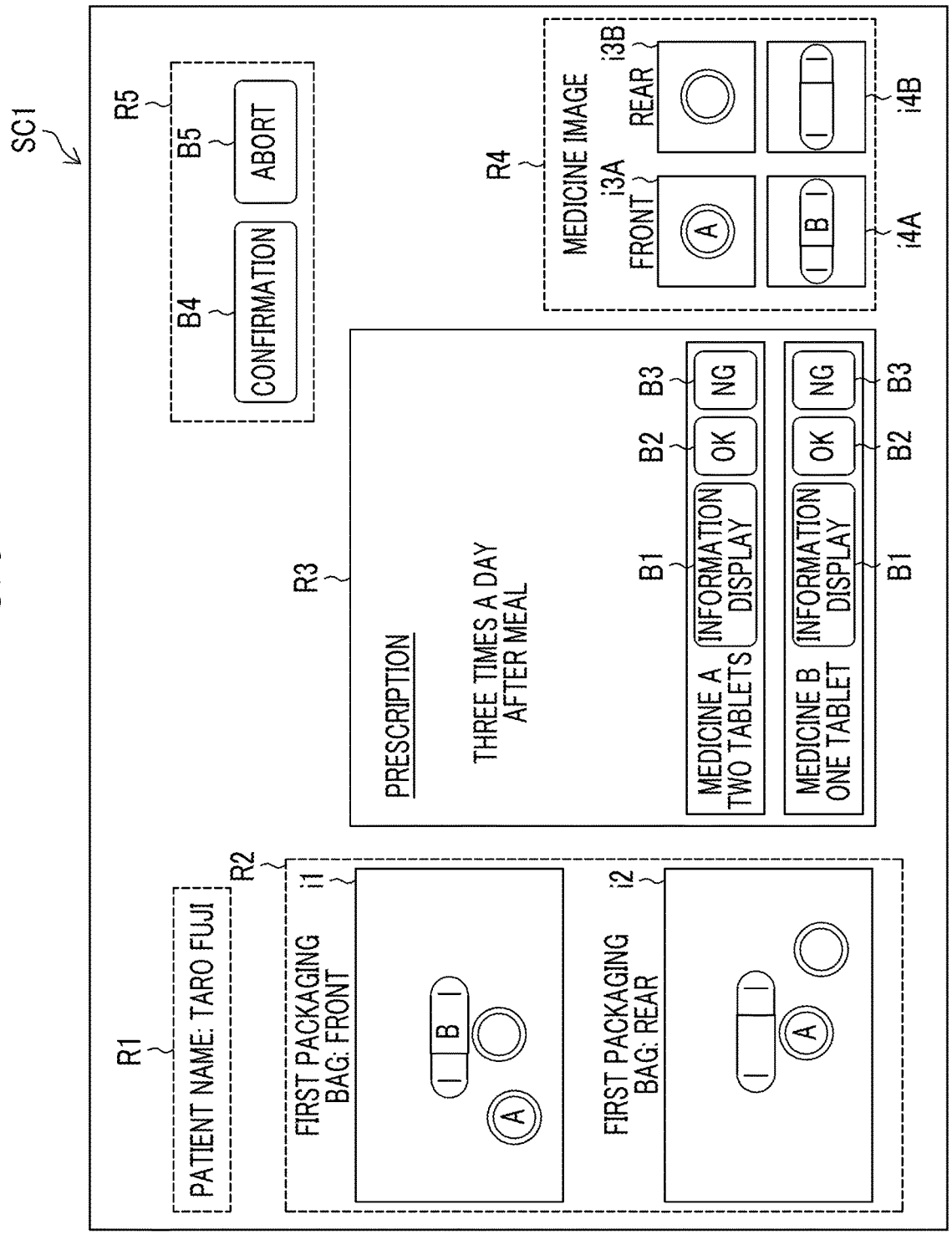
FIG. 6 is a diagram showing an example of a master image registering screen.

FIG. 6 is an example of a screen SC1 to be displayed on the display unit 130. In the example of FIG. 6, the display screen is divided into five regions R1 to R5. The region R1 is a region in which the name of the patient is displayed. The region R2 is a region in which the images of the packaged medicines are displayed. An image i1 is an image captured from above, and an image i2 is an image captured from below. Since the images obtained by imaging the packaged medicines in the plurality of different directions (up and down directions) are displayed, even in a case where it is difficult to perform the collation due to the orientation or overlap of the medicines within the packaging bag, the user (pharmacist) can easily check whether or not the packaged medicines match those written in the prescription, and it is possible to reduce a concern that inappropriate images will be registered as the master image.

It is assumed that "A" and "B" on the images i1 and i2 are respectively the stamps of the medicines A and B and are given on the front surfaces of the medicines. Accordingly, the images i1 and i2 represent the states in which one medicine A and one medicine B face upwards and one medicine A faces downwards.

The region R3 is a region in which prescription data is displayed. In the example of FIG. 6, the usage directions, identification information items (which are the names of the medicines in this example, but are another identification information items), and quantities of the medicines are displayed in this region. Buttons B1 to B3 are displayed in the region R3, and the user can operate these buttons through the operation unit 140. The button B1 is used for displaying the attribute information, the button B2 is used for checking that the packaged medicine matches those written in the prescription, and the button B3 is used for checking that the packaged medicine is not those written in the prescription. The region R4 is a region in which the images (medicine images 120B) of the medicines obtained from the storage unit 120 are displayed. Images i3A and i3B are images obtained by respectively imaging the medicine A from front and rear surfaces, and images i4A and i4B are images obtained by respectively imaging the medicine B from front and rear surfaces. A button B4 for confirming the determination indicating that the medicines packaged in the packaging bag match those written in the prescription, and a button B5 for discarding the captured images in a case where the packaged medicines do not match those written in the prescription are displayed in the region R5.

It is assumed that the images i3A, i3B, i4A, and i4B are obtained for the medicine A and the medicine B through the past medicine inspection.

The user checks whether or not the medicines packaged in the packaging bag match those written in the prescription while referring to the screen SC1 displayed in step S140. The processing unit 110 (determination unit 110E) sets a value of a counter indicating the number of medicines to be 1 (step S150).

The user compares the images i1 and i2 of the medicines displayed in the region R2 with the prescription data displayed in the region R3, and checks whether or not the packaged medicines match those written in the prescription. Since the image i1 obtained by capturing the medicines packaged in the packaging bag from above in the transport direction and the image i2 obtained by capturing the packaged medicines from below in the transport direction are displayed in the region R2, even in a case where it is difficult to check the medicines due to the orientation or overlap of the medicines within the packaging bag, the user can easily check whether or not the packaged medicines match those written in the prescription, and it is possible to reduce a concern that the inappropriate images will be registered as the master image.

Figure 7:
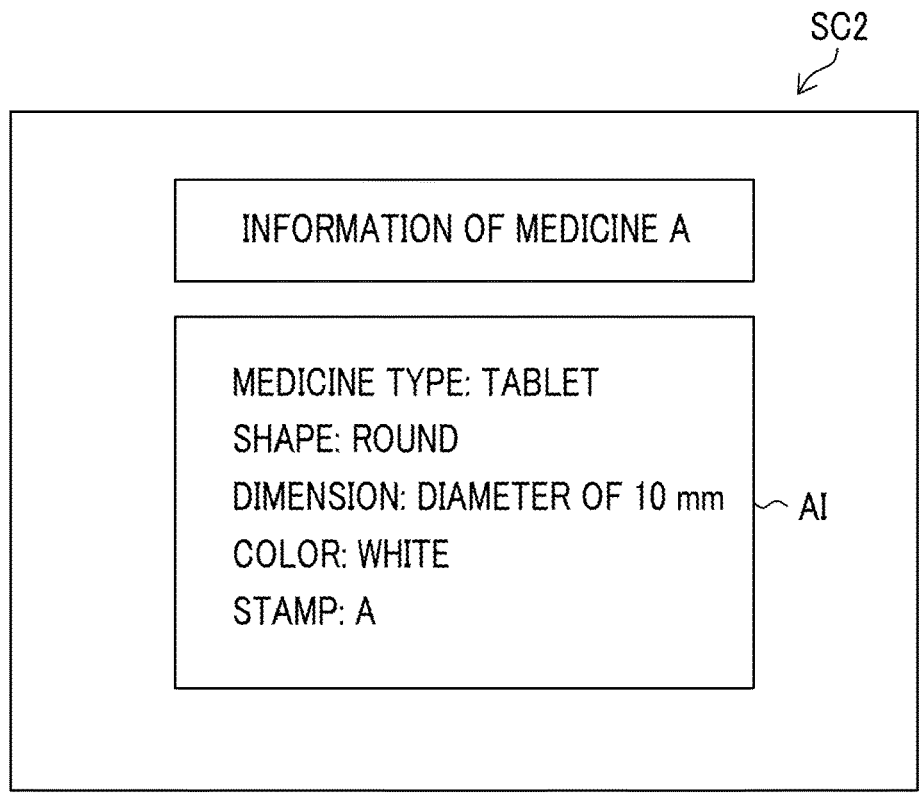
FIG. 7 is a diagram showing a display example of attribute information.

In a case where the button B1 displayed on each medicine described in the prescription is clicked, a screen SC2 shown in FIG. 7 is displayed on the display unit 130. Attribute information items AI (which are the medicine type, shape, dimension, color, and stamp in this example, but the invention is not limited thereto) of the medicine are displayed on the screen SC2 and the user refers to the attribute information items AI, thus, it is possible to easily check whether or not the medicines on the images i1 and i2 match those written in the prescription. Since the images i3A and i3B of the medicine A and the images i4A and i4B of the medicine B to be displayed in the region R4 are the images for which it is checked that the packaged medicines match those written in the prescription, the images i1 and i2 of the packaged medicines are compared with the images i3A, i3B, i4A, and i4B. Accordingly, it is possible to easily check whether or not the packaged medicines match those written in the prescription.

In a case where two medicines A are included on the images i1 and i2, that is, in a case where the user can check that the identification information and quantity of the medicines A match those written in the prescription by using the aforementioned images and information items, the user clicks the button B2 by using the pointing device (not shown) provided on the operation unit 140. By doing this, for an i-th medicine, the determination unit 110E determines that the packaged medicine matches those written in the prescription (Yes in step S160: determination step). The determination unit 110E increases a value i of the counter (step S172), and repeats the determination for all the medicines (while the determination result of step S170 is No). In a case where the determination result is positive for all the medicines (determination result of step S170 is Yes), the master image registering unit 110F registers the images i1 and i2 as the master images (images of a master packaging bag) in the storage unit 120 (master images 120A) (step S180: master image registering step). It is assumed that the identification information items (identification information items 120C) and quantities of the medicines included in the packaging bag stored in association with each other, as the master images.

In step S170, it is assumed that the determination result is positive in a case where the button B2 for OK is clicked for all the medicines and then the button B4 for confirming the determination is clicked.

Figure 8:
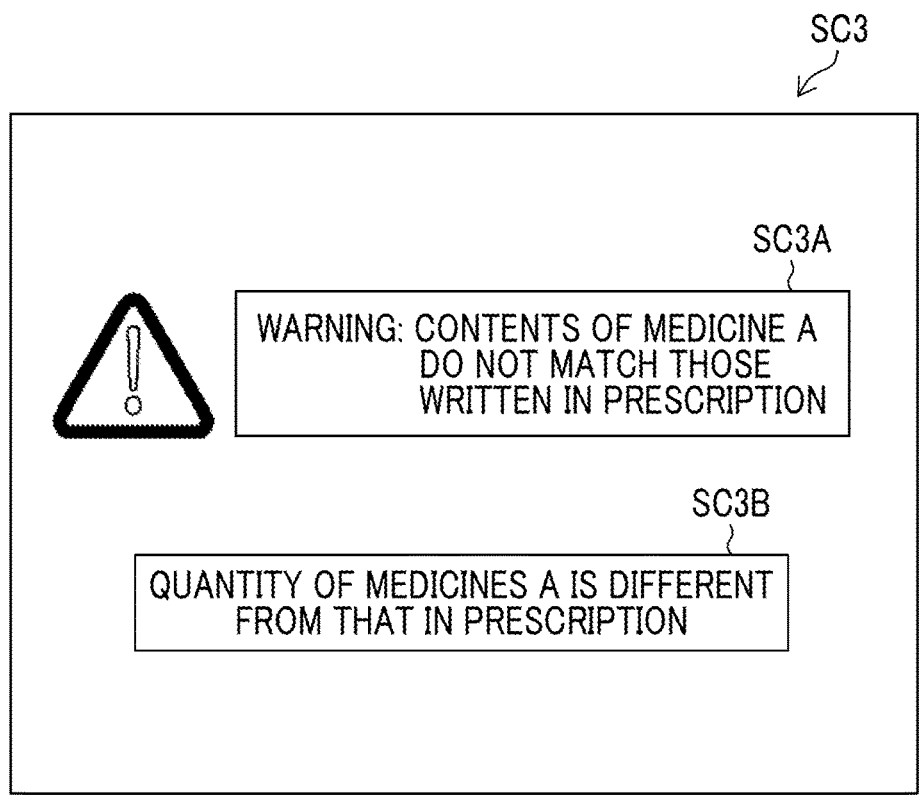
FIG. 8 is a diagram showing an example of a warning output.

In a case where the button B3 is clicked for the medicine A or the medicine B (No in step S160), the warning unit 110H displays a screen SC3 shown in FIG. 8 on the display unit 130 (step S162), and the processing unit discards the images i1 and i2. The processing unit returns to step S100, and obtains images for the next packaging bag. The same is true for a case where the button B5 for aborting is clicked on the screen SC1. The screen SC3 is an example of a warning screen in a case where the contents of the medicine A do not match the contents thereof written in the prescription, and a message SC3A and a message SC3B are displayed.

In a case where it is checked that the packaged medicines match the medicines written in the prescription (the packaged medicines are inspected) through the processes performed until step S180, the processing unit 110 (master image registering unit 110F) stores the images (medicine images 120B) of the individual medicines and the identification information items (identification information items 120C) in association with each other in the storage unit 120 (first storage device) (step S190: storing step). The images stored in step S190 are obtained in step S132 described above, and are displayed in step S140.

As mentioned above, it has been described in the present embodiment that the images i1 and i2 obtained by imaging the packaged medicines in the plurality of different directions (from above and below the packaging bag) are displayed and are compared with the prescription data. The images i3A, i3B, i4A, and i4B for which it is checked that the packaged medicines match those written in the prescription may be displayed and may be collated with the images i1 and i2, and the attribute information items of the medicines may be referred to by clicking the button B1. The captured images are registered as the master images in a case where it is checked that all the medicines match those written in the prescription (the button B4 is clicked after the button B2 is clicked for all the medicines). As stated above, in the present embodiment, it is possible to easily register the master images, and a concern that the inappropriate images will be registered as the master images is low.

In step S200, the collation unit 110G reads out the master images from the storage unit 120 (master images 120A). In a case where the collation is performed subsequently to the processes performed until step S190 (the registration of the master images), the process of step S200 may be omitted. In a case where the master images are read out, the images (second images) of the medicines packaged in the packaging bag are obtained as collating target images (step S210). In a case where the images for the first packaging bag are registered as the master images in the processes performed until step S190, images for the second and subsequent packaging bags are obtained in step S210.

Figure 9:
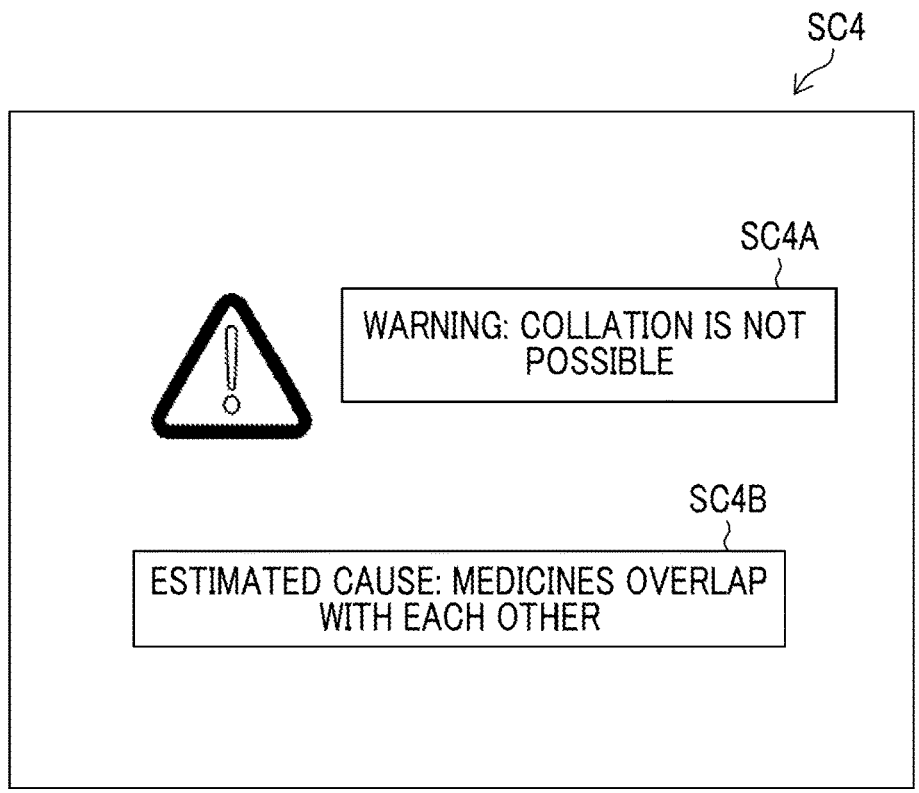
FIG. 9 is a diagram showing another example of the warning output.

In a case where the collating target images are obtained in step S210, the collation unit 110G determines whether or not the master images can be collated with the collating target images (step S220: collation step). In a case where it is not possible to perform the collation due to the overlap of the medicines within the packaging bag, the determination result is negative (No in step S220), the processing unit proceeds to step S222, and the warning unit 110H outputs the warning (warning step). FIG. 9 is an example of a warning output in a case where it is not possible to perform the collation. A message SC4A indicating that it is not possible to perform the collation and a message SC4B indicating an estimated cause (the medicines overlap with each other in the example of FIG. 9) are displayed on a screen SC4. The warning may be output as voice or print without being displayed on the screen.

After the warning is output in step S222, the collation unit 110G determines whether or not to continue the collation (step S224). This determination may be performed based on an instruction input of the user through the operation unit 140, a message (for example, "since the medicines overlap with each other, please separate the medicines") corresponding to the estimated cause by which it is not possible to perform the collation may be displayed on the display unit 130, and the determination result may be positive in a case where the process corresponding to this message is performed. In a case where the process is continued (Yes in step S224), the processing unit returns to step S210, and obtains the images again for the collating target packaging bag. In a case where the process is not continued (No in step S224), the processing unit proceeds to step S260.

In a case where the result of step S220 indicates that it is possible to perform the collation, the processing unit proceeds to step S230, and collates the collating target images with the master images (collation step). For example, in step S230, the collation unit 110G can collate the packaged medicines and the quantities thereof by extracting a feature value of each medicine from the collating target images, extracting a feature value of each medicine from the master images, and comparing the extracted feature values. The shape, size, and color may be used as the feature value of the medicine. Local feature values such as the scale-invariant feature transform (SIFT) may be extracted, and the extracted local feature values may be used in the collation.

Figure 10:
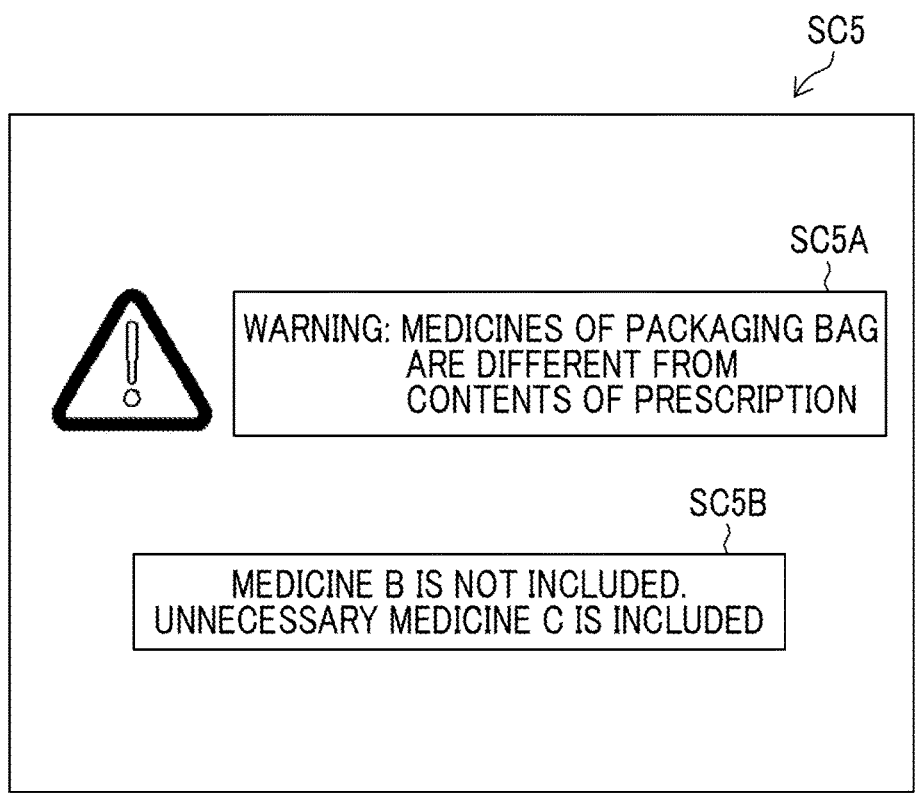
FIG. 10 is a diagram showing still another example of the warning output.

As the result of the collation, in a case where the packaged medicines match those written in the prescription (Yes in step S240), the processing unit proceeds to step S250, and outputs the collation result (for example, "the second packaging bag is packaged as written in the prescription") to the display unit 130. In a case where the packaged medicines do not match those written in the prescription (No in step S240), the processing unit proceeds to step S242 (warning step), outputs the warning, and then proceeds to step S260. FIG. 10 is an example of the outputting of the warning (displaying on the display unit 130) in step S242. A screen SC5 shown in FIG. 10 includes a message SC5A indicating that "the medicines packaged in the packaging bag are different from the contents of the prescription" and a message SC5B indicating that the detailed contents (in this example, "the medicine B is not included in the packaging bag and an unnecessary medicine C is included in the packaging bag) of the warning. The warning may be output as voice or print without being displayed on the screen.

In a case where the collation result (step S250) or the warning (step S242) is output, the collation unit 110G determines whether or not the collation for all the packaging bags is ended (step S260). In a case where the determination result is positive (Yes in step S260), the process is ended. In a case where the determination result is negative (No in step S260), the processing unit returns to step S210, and images images for the next packaging bag.

As described above, according to the inspection support device and the inspection support method according to the present embodiment, it is possible to easily register the master images, and a concern that the inappropriate images will be registered as the master images is low. Accordingly, the user can easily inspect the packaged medicines.

<Another Screen Example at the Time of Registering Master Images>

Next, another example of a screen to be displayed at the time of registering the master images and an operation on the screen will be described. It has been described in the example shown in FIG. 6 that it is checked that the medicines and the quantities thereof match those written in the prescription by displaying the button B2 for each medicine and clicking the button B2. However, in the following example, it is checked whether or not the packaged medicines match those written in the prescription by clicking the corresponding images.

Figure 11:
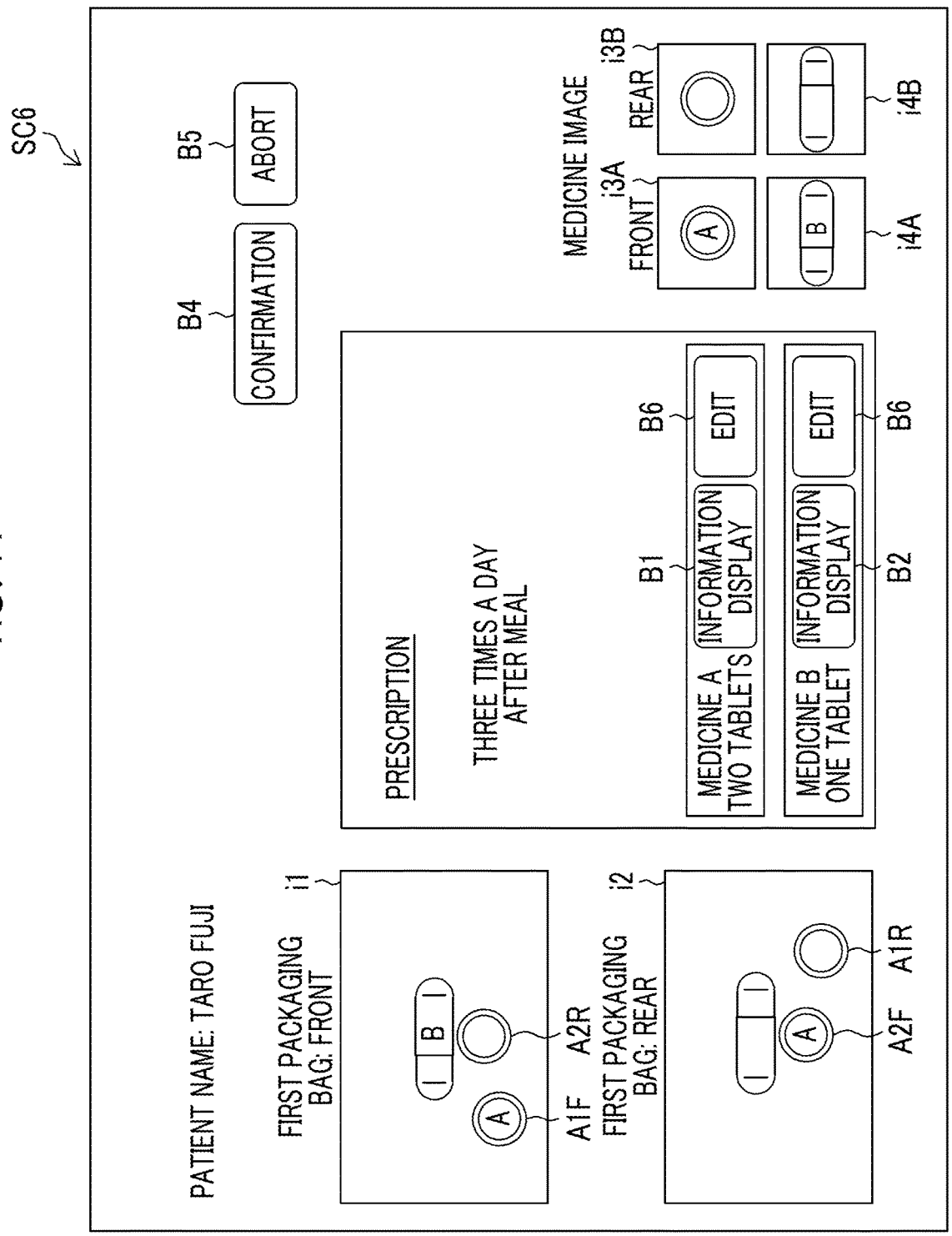
FIG. 11 is a diagram showing another example of a master image registering screen.

FIG. 11 is a diagram showing another example of the display screen. A screen SC6 shown in FIG. 11 is different from the screen SC1 shown in FIG. 6 in that a button B6 for associating the medicine images (checking that the packaged medicines match those written in the prescription) is provided in the region R3, instead of the buttons B2 and B3. In FIG. 11, the assignment of the references to the regions R1 to R5 will be omitted.

In the example shown in FIG. 11, the user clicks the button B6 for the medicine A, and thus, the association of the medicine images is started. Specifically, a region A1F of an image i1 in which the front surface of the medicine A is reflected is clicked, and an image i3A corresponding to this region is subsequently clicked (the order of clicking the region and the image may be reversed). Similarly, a region A1R (the rear surface of the medicine A) of an image i2 corresponding to the region A1F is clicked, and an image i3B corresponding to this region is subsequently clicked (the order of clicking the region and the image may be reversed). The collation unit 110G determines whether or not the clicked images correspond to each other through the comparison of the feature values of the images. Since the images i3A and i3B are the images for which it is checked that the packaged medicine matches that written in the prescription (it is checked that the images correspond to the medicine A), in a case where the determination result is positive, it is checked that one medicine A matching that written in the prescription is included in the packaging bag.

Since two medicines A prescribed in the example of FIG. 11, the user clicks the button B6 again, and associates the medicine images for the second medicine. Specifically, a region A2R of the image i1 in which the rear surface of the medicine A is reflected is clicked, and an image i3B corresponding to this region is subsequently clicked (the order of clicking the region and the image may be reversed). Similarly, a region A2F (a region of the front surface of the medicine A) of the image i2 corresponding to the region A2R is clicked, and an image i3B corresponding to this region is subsequently clicked (the order of clicking the region and the image may be reversed). The determination unit 110E determines whether or not the clicked images correspond to each other through the comparison of the feature values of the images. Since the images i3A and i3B are the images for which it is checked that the packaged medicines match those written in the prescription (it is checked that the images correspond to the medicine A), in a case where the determination result is positive, the determination unit 110E may determine that the identification information and quantity of the medicine A match those written in the prescription (yes in step S160 of FIG. 4: determination step).

The same processes as the processes performed for the medicine A are repeated for the medicine B. In a case where the button B4 is clicked in a state in which it is determined that the identification information and quantity of the medicine B match those written in the prescription (Yes in step S160 of FIG. 4: determination step), the determination unit 110E determines that the identification information items and quantities of all the medicines match those written in the prescription (Yes in step S170 of FIG. 4), and the master image registering unit 110F registers the images i1 and i2 as the master images (step S180: master image registering step). The subsequent collation may be performed similarly to the example described in FIG. 6.

In the present example, it is possible to easily check whether or not the packaged medicines match those written in the prescription by associating the images in this manner Since any of the images i1 and i2 of the packaged medicines and the corresponding images i3A to i4B are the images obtained by the inspection support device 10, it is easy to align imaging conditions, and it is possible to increase the accuracy of the collation. By doing this, in the present example, it is also possible to accurately and easily register the master images, and the user can easily inspect the packaged medicines.

FIG. 12 is a modification example of the example shown in FIG. 11. A screen SC7 shown in FIG. 12 is different from the example of FIG. 11 in that the images (medicine images 120B) of the medicines obtained from the storage unit 120 are displayed as much as the number of medicines written in the prescription. Specifically, since the two medicines A is included in one packaging bag on the prescription, the images of the medicines A are displayed for two medicines (the images i3A and i3B are displayed for one medicine and the images i5A and i5B are displayed for one medicine) so as to correspond to the number of medicines on the screen SC7. For example, the user associates the region A1F with the image i3A, the region A1R with the image i3B, the region A2F with the image i5A, the region A2R with the image i5B on the screen SC7 on which the images of the medicines are displayed in this manner. Accordingly, the determination unit 110E can determine whether or not the packaged medicines match those written in the prescription, and the master image registering unit 110F can register the master images based on the determination result.

As stated above, in the present modification example, since the images of the medicines obtained from the storage unit 120 are displayed so as to correspond to the number of medicines written in the prescription, it is easy to associate the images. Accordingly, it is possible to accurately and easily register the master images, and the user can easily inspect the packaged medicines.

Figure 13:
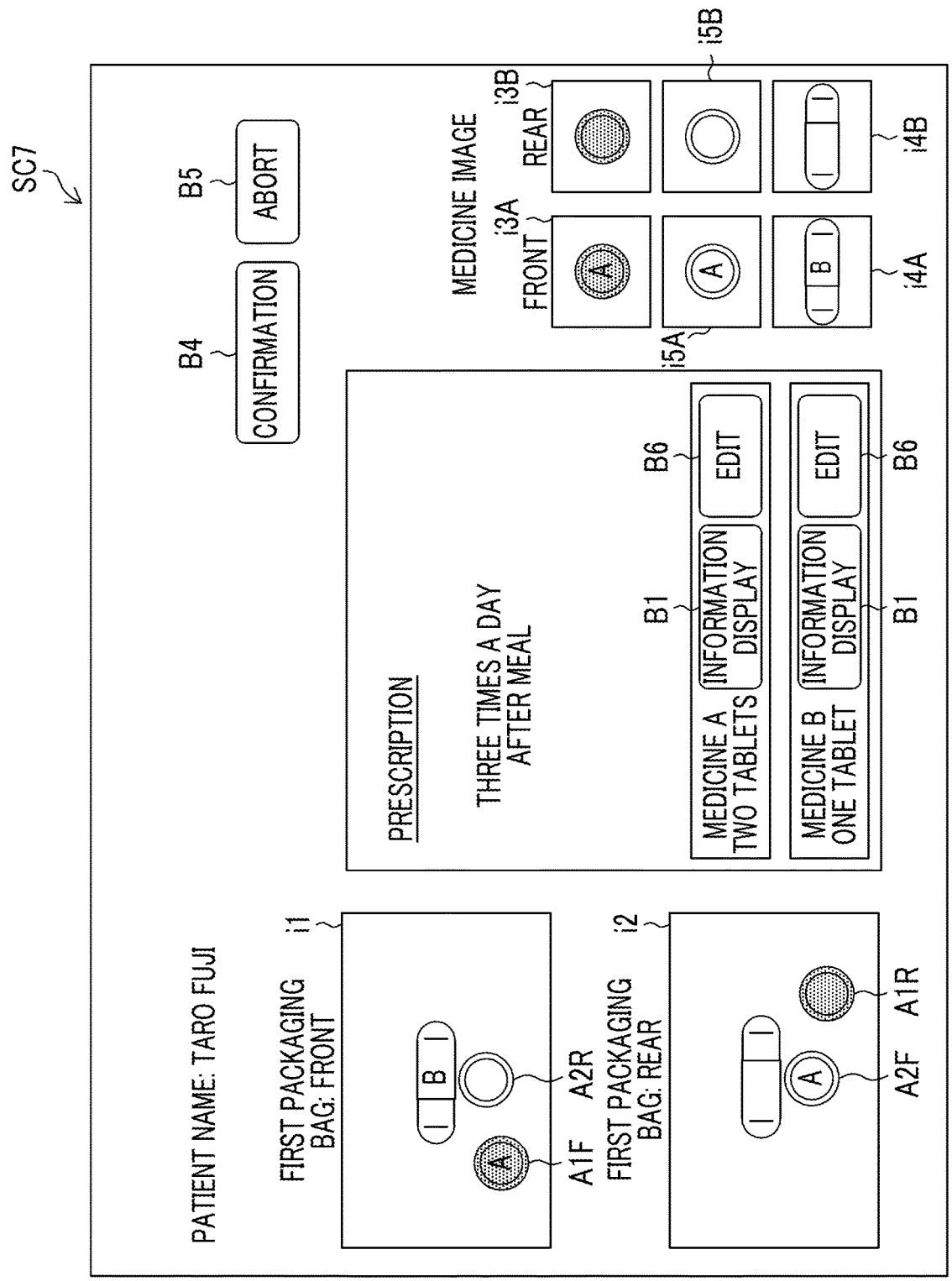
FIG. 13 is a diagram showing a state in which associated medicines are identified and displayed on the master image registering screen.

In the aspects shown in FIGS. 11 and 12, the associated images may be identified and displayed. For example, in a case where the regions A1F and A1R are associated with the images i3A and i3B and it is checked that the packaged medicines match those written in the prescription, the regions A1F and A1R may be colored on the screen SC6 of FIG. 11. On the screen SC7 of FIG. 12, in a case where the regions A1F and A1R are associated with the images i3A and i3B and it is checked that the packaged medicines match those written in the prescription, the regions A1F and A1R and the images i3A and i3B may be colored. In a case where the regions A2F and A2R are associated with the images i5A and i5B and it is checked that the medicines match those written in the prescription, the regions A1F and A1R and the images i5A and i5B may be colored. FIG. 13 is a diagram showing an example of such identification display, and shows a state in which the regions A1F and A1R are associated with the images i3A and i3B, it is checked that the packaged medicines match those written in the prescription, and the regions A1F and A1R and the images i3A and i3B are colored on the screen example of FIG. 12. Such identification display is performed, and thus, it is possible to accurately and easily register the master images. Accordingly, the user can easily inspect the packaged medicines.

The present invention is not limited to the above-described embodiment, other examples, and modification example, and may be modified without departing from the spirit of the present invention.

EXPLANATION OF REFERENCES

10: inspection support device
102: camera
104: camera
106: reader
110: processing unit
110A: image obtaining unit
110B: information extracting unit
110C: attribute information obtaining unit
110D: display controller
110E: determination unit
110F: master image registering unit
110G: collation unit
110H: warning unit
120: storage unit
120A: master image
120B: medicine image
120C: identification information
120D: attribute information
120E: prescription information
130: display unit
140: operation unit
A1F: region
A1R: region
A2F: region
A2R: region
AI: attribute information
B1: button
B2: button
B3: button
B4: button
B5: button
B6: button
R1: region
R2: region
R3: region
R4: region
R5: region
S100 to S260: steps of inspection support method
SC1: screen
SC2: screen
SC3: screen
SC4: screen
SC5: screen
SC6: screen
SC7: screen
SC3A: message
SC3B: message
SC4A: message
SC4B: message
SC5A: message
SC5B: message
i1: image
i2: image
i3A: image
i3B: image
i4A: image
i5A: image
i5B: image

What is claimed is:

1. An inspection support method comprising:
obtaining first images which are images of packaged medicines;
extracting identification information items and quantities of medicines written in a prescription;
displaying the obtained first images and the extracted identification information items and quantities on a display device;
determining whether or not identification information items and quantities of the packaged medicines match the displayed identification information items and quantities based on an instruction input of a user including a) displaying for each medicine in the written prescription, one or more buttons for verifying a medicine type and quantity of the medicine type; b) accepting a user input for verification via the one or more buttons, and c) providing a positive determination when it is determined that the user activates a positive one of the buttons and providing a negative determination when the user activates a negative one of the buttons, the user verification occurring before a second matching performed by a processor;

registering the first images as master images in a case where the determination result is positive for all the medicines written in the prescription; and collating whether or not the medicines packaged in each packaging bag match the medicines written in the prescription based on the registered master images and second images which are images obtained for each packaging bag.

2. The inspection support method according to claim 1, further comprising:

storing the images and the identification information items in association with each other for the medicines included in the inspected packaging bag in a first storage device; and obtaining the images of the medicines written in the prescription while referring to the first storage device based on the extracted identification information items, wherein the images of the medicines obtained are displayed.

3. The inspection support method according to claim 1, further comprising:

obtaining attribute information items of the medicines written in the prescription while referring to a second storage device that stores the attribute information items of the medicines based on the extracted identification information items, wherein the obtained attribute information items are displayed on the display device.

4. The inspection support method according to claim 3, wherein the attribute information includes at least one of a medicine type, a shape, a dimension, a color, or a stamp of the medicine.

5. The inspection support method according to claim 1, wherein a plurality of images obtained by imaging the packaged medicines in a plurality of different directions is obtained as the first images, and the plurality of images obtained as the first images is displayed.

6. The inspection support method according to claim 1, further comprising:

outputting a warning in a case where the collating is not able to be performed and the medicines packaged in each packaging bag do not match the medicines written in the prescription as the result of the collating.

7. An inspection support device comprising:

at least one processor circuit configured to:

obtain first images which are images of packaged medicines;

extract identification information items and quantities of medicines written in a prescription;

control a display to display the obtained first images and the extracted identification information items and quantities;

determine whether or not identification information items and quantities of the packaged medicines match the displayed identification information items and quantities based on an instruction input of a user including a) displaying for each medicine in the written prescription, one or more buttons for verifying a medicine type and quantity of the medicine type; b) accepting a user input for verification via the one or more buttons, and c) providing a positive determination when it is determined that the user activates a positive one of the buttons and providing a negative determination when the user activates a negative one of the buttons, the user verification occurring before a second matching performed by the processor circuit;

register the first images as master images in a case where the determination result is positive for all the medicines written in the prescription; and collate whether or not the medicines packaged in each packaging bag match the medicines written in the prescription based on the registered master images and second images which are images obtained for each packaging bag.

* * * * *